(12) United States Patent
Borchert et al.

(10) Patent No.: US 11,692,633 B2
(45) Date of Patent: Jul. 4, 2023

(54) PINCH CLAMP AND MOUNT

(71) Applicant: MASTERFLEX, LLC, Radnor, PA (US)

(72) Inventors: Sean Michael Borchert, Crystal Lake, IL (US); Gregg Eugene Johnson, River Grove, IL (US); Eric Adam Nofziger, Lombard, IL (US)

(73) Assignee: Masterflex, LLC, Radnor, PA (US)

( * ) Notice: Subject to any disclaimer, the term of this patent is extended or adjusted under 35 U.S.C. 154(b) by 0 days.

(21) Appl. No.: 17/670,996

(22) Filed: Feb. 14, 2022

(65) Prior Publication Data
US 2022/0390023 A1 Dec. 8, 2022

Related U.S. Application Data

(60) Provisional application No. 63/196,780, filed on Jun. 4, 2021.

(51) Int. Cl.
*F16K 7/04* (2006.01)

(52) U.S. Cl.
CPC ..................... *F16K 7/04* (2013.01)

(58) Field of Classification Search
CPC ........................................ F16K 7/04
USPC ............................................. 251/9
See application file for complete search history.

(56) References Cited

U.S. PATENT DOCUMENTS

| | | | | | |
|---|---|---|---|---|---|
| 3,612,475 A | * | 10/1971 | Dinger | ............... | A61B 17/122 251/9 |
| 3,698,681 A | * | 10/1972 | Lacey | ............... | A61M 39/284 251/10 |
| 3,822,052 A | * | 7/1974 | Lange | ............... | A61B 17/122 251/10 |
| 3,874,042 A | * | 4/1975 | Eddleman | ............... | F16K 7/04 251/10 |
| 3,942,228 A | * | 3/1976 | Buckman | ............... | A61M 39/284 251/10 |

(Continued)

FOREIGN PATENT DOCUMENTS

EP 0762034 A1 3/1997

OTHER PUBLICATIONS

Extended European Search Report for corresponding EP Patent Application No. 22174755.3 dated Oct. 10, 2022. 8 pages.

*Primary Examiner* — Craig M Schneider
*Assistant Examiner* — Frederick D Soski
(74) *Attorney, Agent, or Firm* — Faegre Drinker Biddle & Reath LLP

(57) ABSTRACT

A pinch clamp and mount are provided. The pinch clamp includes a first member and second member including rounded pinch surfaces. The second member is pivotably coupled to the first member at a first end. A threaded shaft is pivotably coupled to a second end of the first member. A second end of the second member includes a seat configured to receive the threaded shaft and a nut thereon. The seat includes protrusions at the second end that prevent the nut from sliding out of the seat. The mount includes a body having a flat bottom surface. An internal wall defines a through hole in the flat bottom surface. Two guide rails on a top surface of the body define a central slot configured to receive the clamp. A pair of keyed slots within the two guide rails are configured to receive a pair of keyed projections on the clamp.

12 Claims, 18 Drawing Sheets

(56) References Cited

U.S. PATENT DOCUMENTS

| | | | | |
|---|---|---|---|---|
| 4,053,135 A * | 10/1977 | Saliaris | F16K 7/063 | 251/10 |
| 4,091,815 A * | 5/1978 | Larsen | A61B 17/122 | 251/10 |
| 4,193,174 A * | 3/1980 | Stephens | A61M 25/02 | 128/207.18 |
| 4,235,412 A * | 11/1980 | Rath | A61M 39/284 | 251/10 |
| 4,453,295 A * | 6/1984 | Laszczower | A61M 39/284 | 251/10 |
| 4,469,227 A * | 9/1984 | Faust | F25D 25/005 | 383/119 |
| 4,588,160 A * | 5/1986 | Flynn | A61M 39/284 | 251/10 |
| 4,589,626 A * | 5/1986 | Kurtz | A61M 39/288 | 251/10 |
| 4,643,389 A * | 2/1987 | Elson | A61M 39/284 | 251/10 |
| 4,673,161 A * | 6/1987 | Flynn | A61M 39/284 | 251/10 |
| 4,807,622 A * | 2/1989 | Ohkaka | A61M 39/284 | 606/167 |
| 5,320,389 A | 6/1994 | Dupont | | |
| 5,401,256 A * | 3/1995 | Stone | A61M 39/287 | 604/246 |
| 5,423,769 A | 6/1995 | Jonkman et al. | | |
| 5,474,268 A | 12/1995 | Yu | | |
| 5,817,116 A * | 10/1998 | Takahashi | F16L 55/10 | 606/167 |
| 5,865,813 A * | 2/1999 | DeKalb | A61M 39/284 | 604/250 |
| D427,307 S * | 6/2000 | Guala | D24/129 | |
| 6,089,527 A * | 7/2000 | Utterberg | A61M 39/284 | 251/10 |
| 6,113,062 A * | 9/2000 | Schnell | A61M 39/284 | 251/10 |
| D431,650 S * | 10/2000 | Guala | D24/129 | |
| 6,161,812 A * | 12/2000 | Guala | A61M 39/284 | 251/9 |
| 6,234,448 B1 | 5/2001 | Porat | | |
| 6,435,568 B1 | 8/2002 | Fukano et al. | | |
| 6,592,558 B2 * | 7/2003 | Quah | A61M 39/284 | 128/912 |
| 6,644,618 B1 * | 11/2003 | Balbo | A61M 39/284 | 251/9 |
| 6,708,377 B2 | 3/2004 | Maunder | | |
| 6,742,760 B2 * | 6/2004 | Blickhan | F16K 7/06 | 251/11 |
| 6,796,586 B2 | 9/2004 | Werth | | |
| 7,066,441 B2 | 6/2006 | Warburton | | |
| 7,137,611 B2 | 11/2006 | Aulicino | | |
| 7,384,078 B2 | 6/2008 | Cobb et al. | | |
| 7,559,525 B2 | 7/2009 | Grimes | | |
| 8,028,378 B2 | 10/2011 | Shor et al. | | |
| 8,177,187 B2 | 5/2012 | Feast | | |
| 8,256,802 B2 | 9/2012 | Werth | | |
| 8,262,639 B2 | 9/2012 | Mathias et al. | | |
| 8,328,457 B2 | 12/2012 | Werth | | |
| 8,328,763 B2 * | 12/2012 | Traversaz | A61M 5/14244 | 604/250 |
| 8,662,542 B2 | 3/2014 | Werth | | |
| 8,888,398 B2 | 11/2014 | Werth | | |
| 8,940,228 B2 * | 1/2015 | Hlavinka | A61M 39/286 | 422/186.04 |
| 9,151,420 B2 | 10/2015 | Mckiernan | | |
| 9,377,015 B2 * | 6/2016 | Traversaz | A61M 39/284 | |
| 9,605,782 B2 | 3/2017 | Werth | | |
| 9,677,674 B2 | 6/2017 | Spink et al. | | |
| 9,879,813 B2 | 1/2018 | Meola et al. | | |
| D833,265 S | 11/2018 | Meola et al. | | |
| 10,384,049 B2 | 8/2019 | Stanton et al. | | |
| 10,556,301 B2 | 2/2020 | Baker et al. | | |
| 10,688,296 B2 * | 6/2020 | Heriot | A61F 9/00781 | |
| 2002/0169423 A1 | 11/2002 | Zoltan et al. | | |
| 2006/0071187 A1 | 4/2006 | Aulicino | | |
| 2011/0163533 A1 | 7/2011 | Snyder et al. | | |
| 2013/0249212 A1 | 9/2013 | McKiernan | | |
| 2015/0198272 A1 | 7/2015 | Meola et al. | | |
| 2015/0250995 A1 * | 9/2015 | Davis | F16K 7/04 | 604/250 |
| 2015/0330516 A1 * | 11/2015 | Spink | F16K 37/0008 | 251/8 |
| 2016/0053926 A1 | 2/2016 | Whitaker | | |
| 2019/0091463 A1 | 3/2019 | Kramer et al. | | |

* cited by examiner

PINCH CLAMP AND MOUNT

CROSS-REFERENCE TO RELATED APPLICATIONS

This application claims priority to U.S. Provisional Application No. 63/196,780 titled "PINCH CLAMP AND MOUNT," filed Jun. 4, 2021, which is assigned to the assignee hereof, and incorporated herein by reference in its entirety.

INTRODUCTION

The present disclosure generally relates to pinch clamps for tubing.

BACKGROUND

A pinch clamp may be used to stop the flow of fluid though a flexible tube. For example, a pinch clamp may be located between a fluid source and a fluid destination. The pinch clamp may stop the flow of fluid between processes, for example, when containers are being changed or a pump is being configured.

Conventional pinch clamps may include a threaded shaft and a nut that close the pinch clamp. The threaded shaft may pivot into position and the nut may be tightened. A user may be unsure whether a clamp is fully closed. Additionally, as the nut extends from the surface of the pinch clamp, there may be risk of movement of the nut. In some cases, the tubing and the attached pinch clamp may be free to move, which may result in unintentional loosening of the pinch clamp and/or tangling or undesirable positioning of the tubing. .

Accordingly, there is a need for pinch clamps that are easy to use in a medical or laboratory environment.

SUMMARY

The following presents a simplified summary of one or more aspects of the invention in order to provide a basic understanding of such aspects. This summary is not an extensive overview of all contemplated aspects, and is intended to neither identify key or critical elements of all aspects nor delineate the scope of any or all aspects. Its purpose is to present some concepts of one or more aspects in a simplified form as a prelude to the more detailed description that is presented later.

In one aspect, the disclosure provides a pinch clamp. The pinch clamp may include a first member including a first rounded pinch surface. The pinch clamp may include a second member having an opposing second rounded pinch surface and pivotably coupled to the first member at a first end of the first member. The pinch clamp may include a threaded shaft pivotably coupled to a second end of the first member. A second end of the second member includes a seat configured to receive the threaded shaft and a nut threaded onto the threaded shaft. The seat includes protrusions at the second end that prevent the nut from sliding out of the seat past the second end.

In some implementations, the pinch clamp may include a pair of keyed projections extending from the second end toward the first end along a bottom surface of the first member on opposite sides of the first rounded pinching surface.

In some implementations, the pinch clamp may include a mount including: an internal wall defining a through hole; two guide rails defining a central slot configured to receive the first member; and a pair of keyed slots within the two guide rails configured to receive the pair of keyed projections.

In some implementations, the pinch clamp may include corresponding guide indentations and guide projections located on a bottom surface of the first member and a top surface of the mount.

In some implementations, the mount includes a sloped surface configured to receive the first end of the first member. The sloped surface may include alignment tabs and the first member includes slots configured to receive the alignment tabs. The sloped surface may include a recess configured to receive a curved portion of the first end of the second member.

In another aspect, the disclosure provides a mount for a clamp. The mount may include a body having a flat bottom surface. The mount may include an internal wall defining a through hole in the flat bottom surface. The mount may include two guide rails on a top surface of the body defining a central slot configured to receive a clamp. The mount may include a pair of keyed slots within the two guide rails configured to receive a pair of keyed projections on the clamp.

In another aspect, the disclosure provides A clamp and mount system configured to have the clamp interchangeably mounted thereto. The system may include a mount having a body with a bottom surface configured to be mounted to a mounting surface. The guiding member may further include a slot configured to receive the clamp. The system may further include a pinch clamp having a first member including a first pinch surface. The system may further include a second member having an opposing pinch surface and pivotably coupled to the first member at a first end of the first member. The system may further include a threaded shaft coupled to a second end of the first member. A second end of the second member may include a seat configured to receive the threaded shaft and a nut threaded onto the threaded shaft.

In another aspect, the disclosure provides a clamp. The clamp may include a first member having a first engagement surface and a second member having an opposing second engagement surface. The second member may be pivotably coupled to the first member at a first end of the first member. The clamp may include a threaded shaft pivotably coupled to a second end of the first member. A second end of the second member may include a seat configured to receive the threaded shaft and a nut threaded onto the threaded shaft, the seat including protrusions at the second end that prevent the nut from sliding out of the seat past the second end.

In some implementations, the clamp (e.g., pinch clamp) may include a pair of keyed projections extending from the second end toward the first end along a bottom surface of the first member on opposite sides of the first rounded pinching surface.

These and other aspects of the invention will become more fully understood upon a review of the detailed description, which follows.

DETAILED DESCRIPTION

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known components are shown in block diagram form in order to avoid obscuring such concepts.

In an aspect, the disclosure provides for a pinch clamp and mount. The pinch clamp includes a first member pivotably coupled to a second member at a first end. A second end of the first member is pivotably coupled to a threaded shaft. A second end of the second member includes a seat for receiving the threaded shaft and a nut threaded onto the threaded shaft. The seat includes protrusions at the second end. The protrusions prevent the nut from sliding out of the seat past the second end. The first member and the second member include opposed rounded pinching surfaces.

The pinch clamp may be attached to a mount. The mount includes an interior wall defining a through hole. A fastener (e.g., a screw or bolt) may be received in the through hole to attach the mount to a surface. The mount includes guide protrusions extending from a top surface. The mount includes a central slot for receiving a bottom surface of the first member of the pinch clamp. The central slot is defined by side rails including keyed slots for receiving keyed projections of the first member of the pinch clamp. The mount may include a sloped surface that contacts the first end of the pinch clamp. The sloped surface may include alignment tabs that are received in the first end of the pinch clamp. The sloped surface may include a curved notch that allows the second member to pivot while the pinch clamp is mounted.

Figure 1:
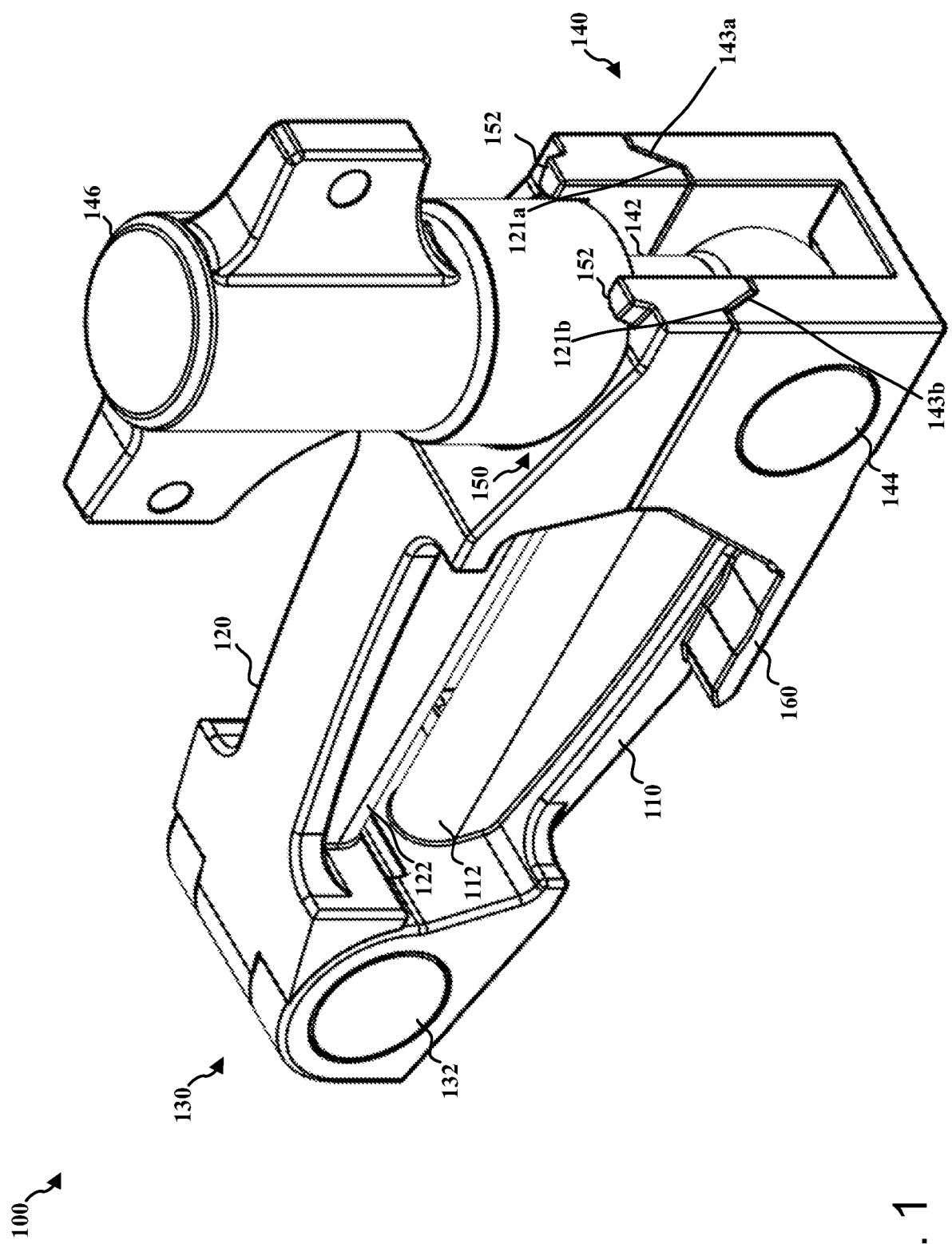
FIG. 1 is perspective view of an example pinch clamp, according to an aspect of the disclosure.
Figure 2:
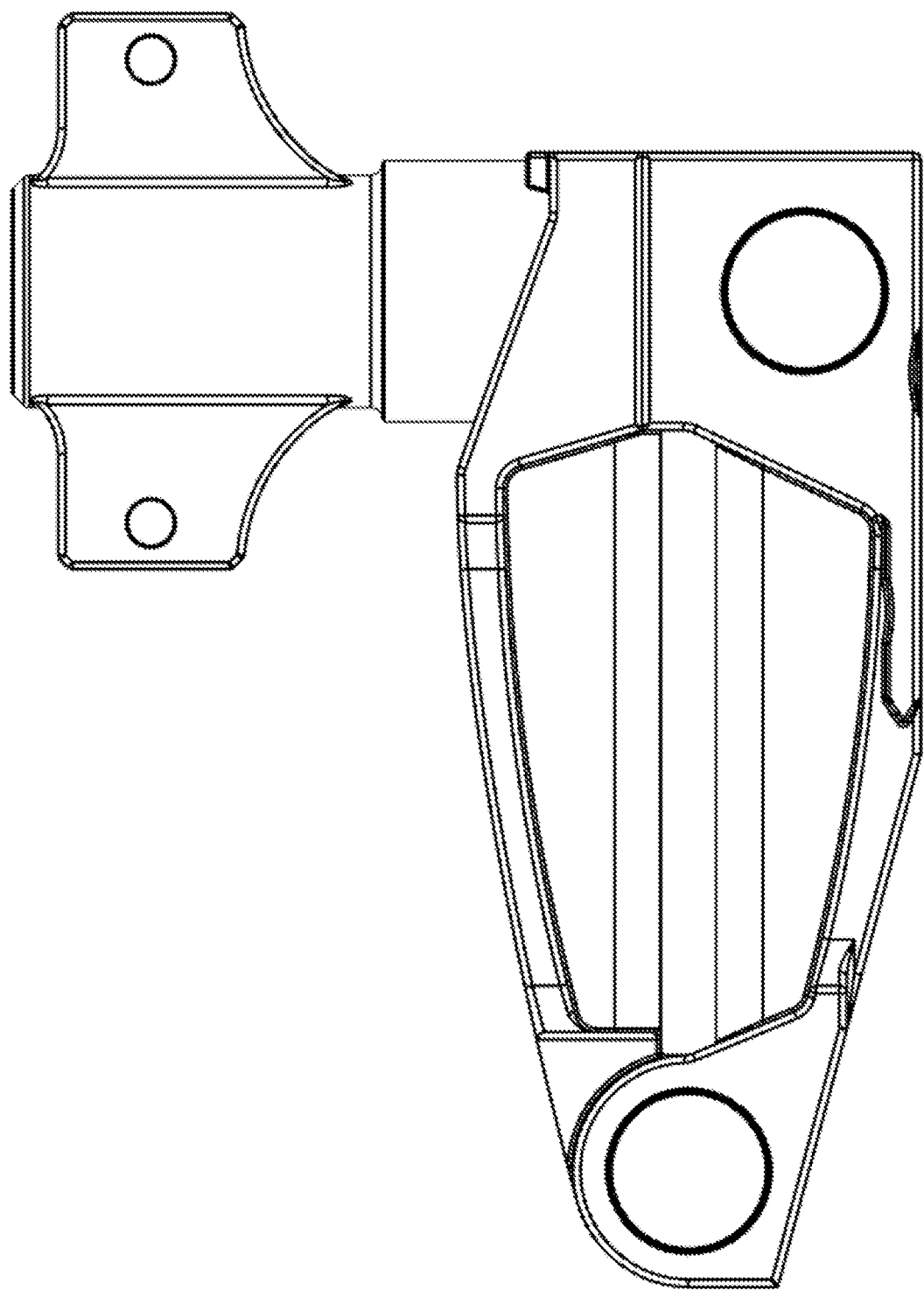
FIG. 2 is a front view of the design shown in FIG. 1.
Figure 3:
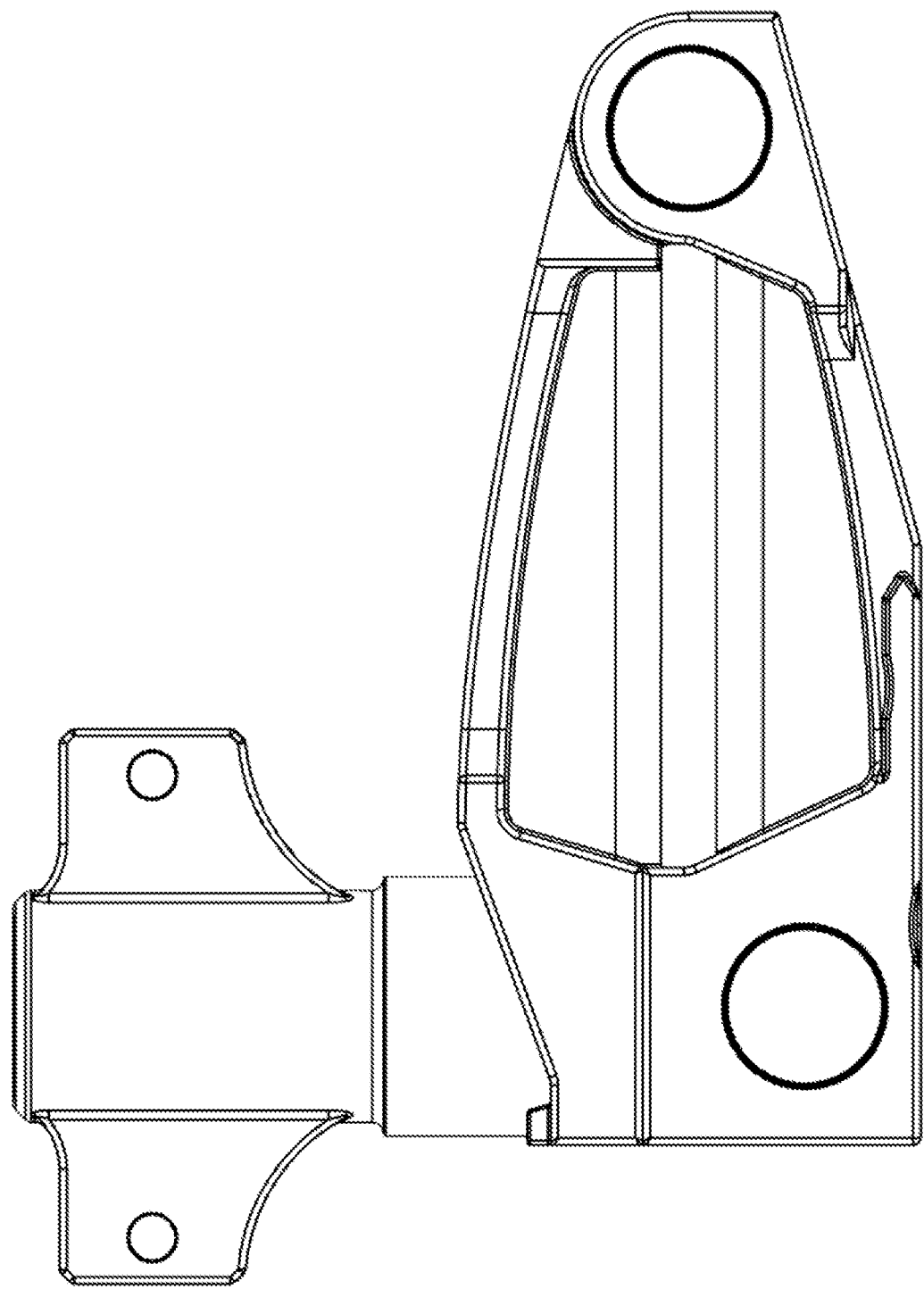
FIG. 3 is a rear view of the design shown in FIG. 1.
Figure 4:
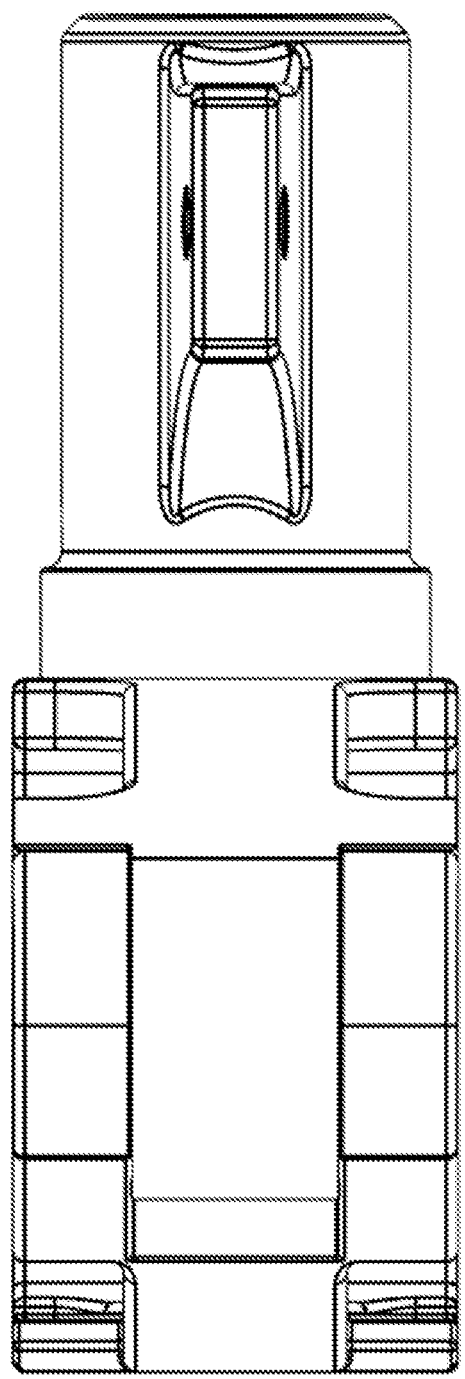
FIG. 4 is a right side view of the design shown in FIG. 1.
Figure 5:
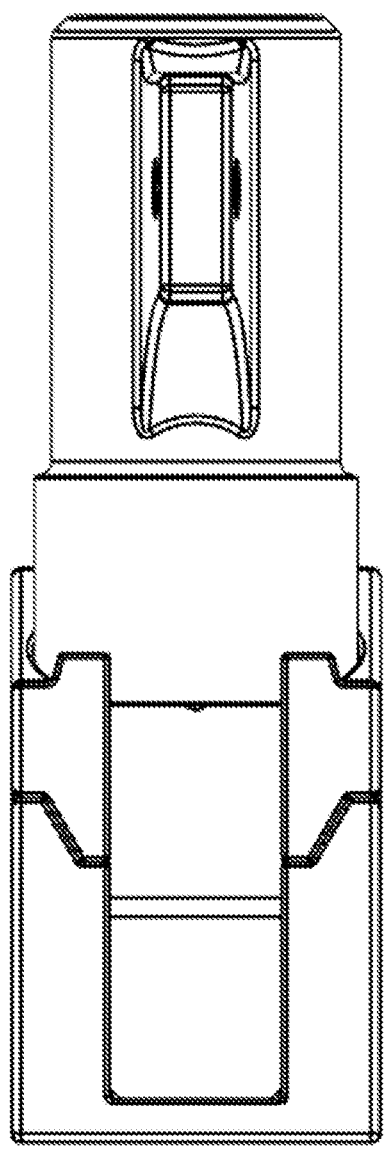
FIG. 5 is a left side view of the design shown in FIG. 1.
Figure 6:
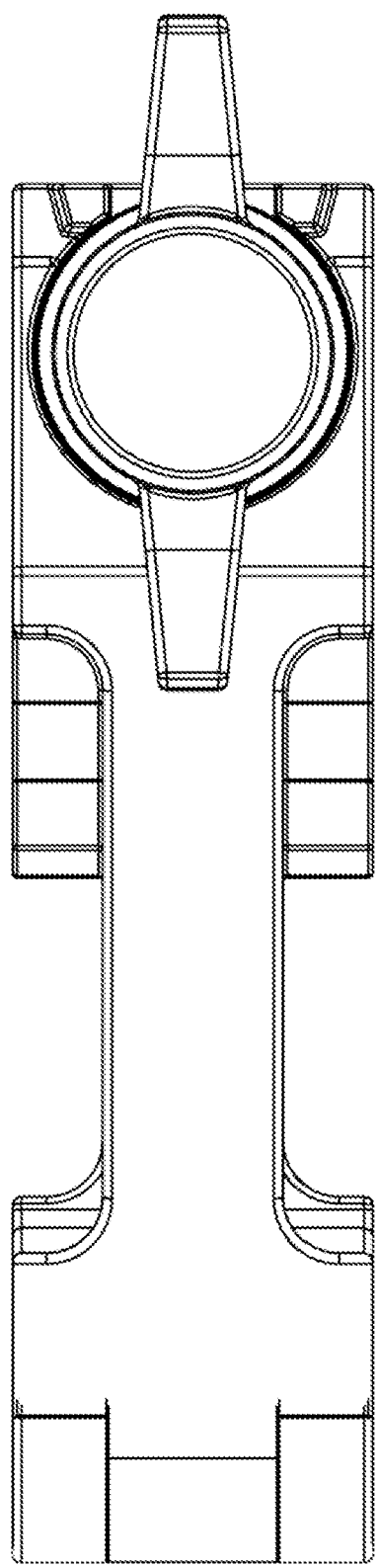
FIG. 6 is a top view of the design shown in FIG. 1.
Figure 8:
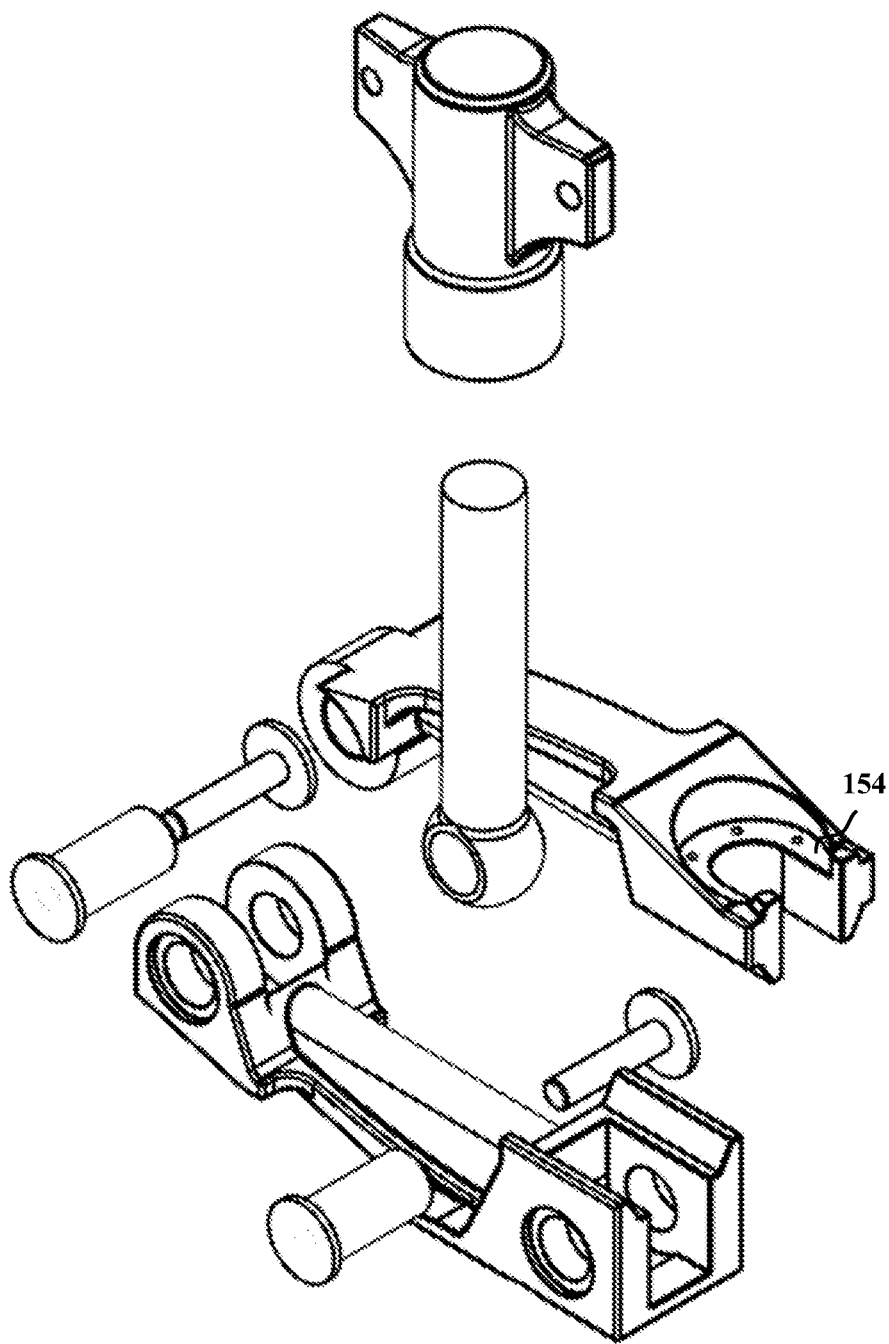
FIG. 8 is an exploded view of the example pinch clamp shown in FIG. 1.

FIG. 1 is perspective view of an example pinch clamp 100. The pinch clamp 100 includes a first member 110 including a first rounded pinch surface 112. The pinch clamp 100 includes a second member 120 including a second rounded pinch surface 122. The first member 110 and the second member 120 may be pivotably coupled at a first end 130 of the first member 110 and the second member 120. For example, the first member 110 may be coupled to the second member 120 via a pin 132 that passes through a respective opening in each of the first member 110 and the second member 120. Other example pivot mechanisms (e.g., hooks or protrusions) may be formed at the first end 130. The pinch clamp 100 may include a threaded shaft 142 pivotably coupled to a second end 140 of the first member 110. For example, the threaded shaft 142 may be coupled to the first member 110 via a pin 144 or a structure of the first member 110 and/or the threaded shaft 142. In an aspect, a second end 140 of the second member 120 includes a seat 150 configured to receive the threaded shaft 142 and a nut 146 threaded onto the threaded shaft. For example, the seat 150 may include an end wall defining a U-shaped opening at the second end 140. In some implementations, the nut 146 may be a wing nut with handles to facilitate manual turning of the nut 146. The top surface of the seat 150 may include a partially annular flat surface 154 (best seen in FIG. 8) that contacts a bottom surface of the nut 146. The partially annular flat surface 154 and/or the bottom surface of the nut 146 may include corresponding textures (e.g., round depressions and projections) that resist movement when the nut 146 is fully tightened. The seat 150 may include inclined walls partially surrounding the partially annular flat surface to guide the nut 146 to the partially annular flat surface 154 as the nut is tightened on the threaded shaft. The seat 150 may include protrusions 152 at the second end 140 that prevent the nut 146 from sliding out of the seat 150 past the second end 140. For example, the protrusions 152 may extend upward from a top surface of the second member 120 on each side of the seat 150. An interface between the first member 110 and the second member 120 at the second end 140 may include corresponding first inclined surface(s) 143a and 143b and second inclined surfaces 121a and 121b to guide the first member 110 and second member 120 into alignment.

In use, the pinch clamp 100 may start in an open position with the threaded shaft 142 pivoted out of the seat 150 and the nut 146 loosened to clear the protrusions 152. The first member 110 and the second member 120 may pivot at the first end 130. A user may insert one or more flexible tubes between the curved pinching surfaces 112 and 122. A smallest distance between the curved pinching surfaces 112 and 122 may prevent flow of fluid within the one or more tubes. For instance, the tubing and/or the pinch clamp 100 may be selected such that the distance between the curved pinching surfaces 112 and 122 is approximately two times a wall thickness of the tubing. The first member 110 and second member 120 may be manually closed around the one or more tubes and the threaded shaft 142 may be pivoted into the seat 150. The nut 146 may be tightened to bring the bottom surface of the nut into contact with the partially annular flat surface of the seat 150. The inclined sides of the seat 150 and/or protrusions 152 may guide the nut 146 into contact with the partially annular flat surface 154 of the seat 150. With the nut 146 in contact with the partially annular flat surface 154 of the seat 150, the protrusions 152 prevent the nut 146 from exiting the seat 150 even if a force is applied to the nut 146 in the direction toward the second end 140.

Figure 7:
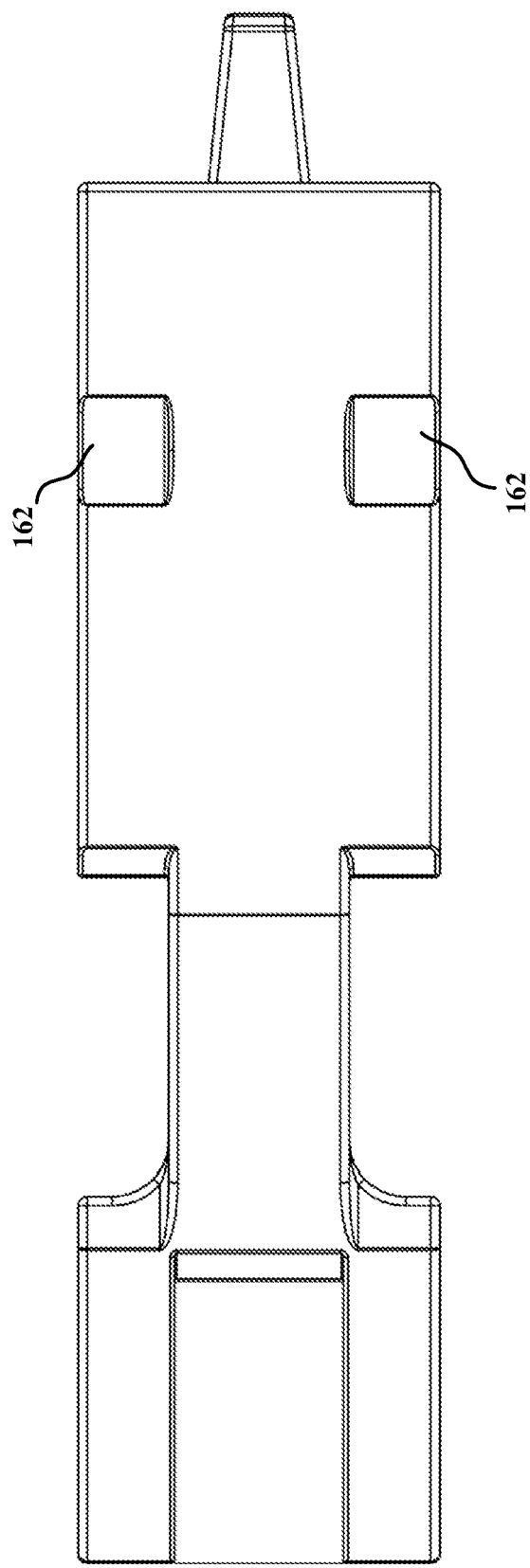
FIG. 7 is a bottom view of the design shown in FIG. 1.
Figure 9:
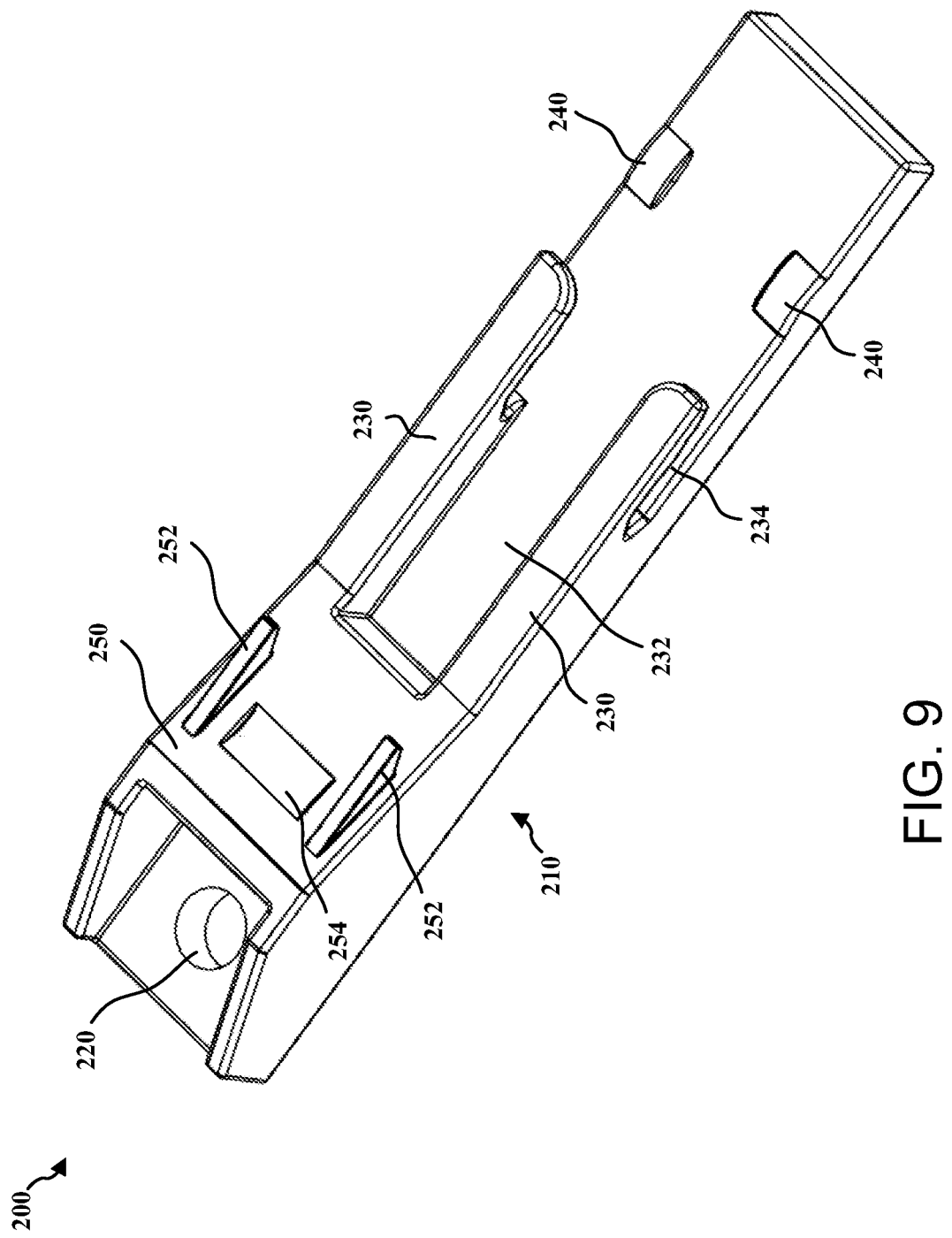
FIG. 9 is perspective view of an example clamp mount, according to an aspect of the disclosure.
Figure 10:
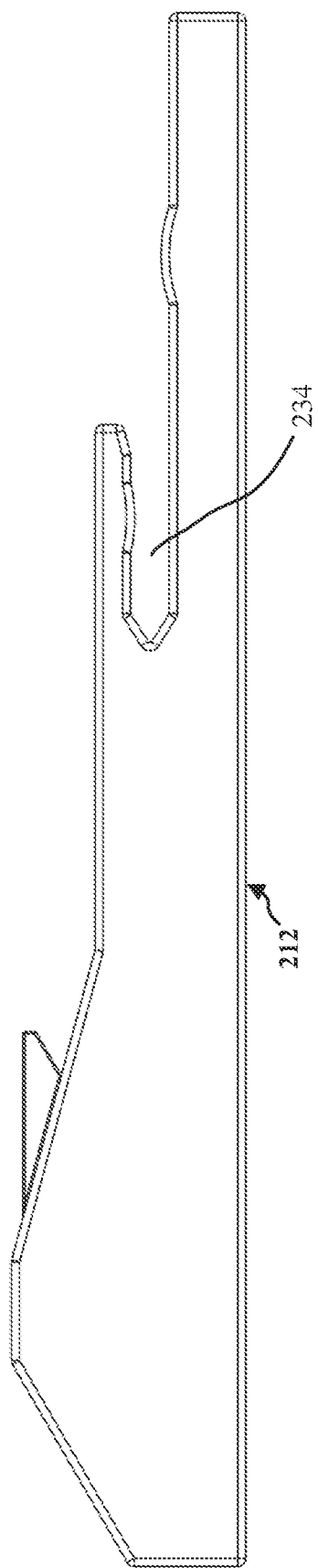
FIG. 10 is a front view of the design shown in FIG. 1.
Figure 11:
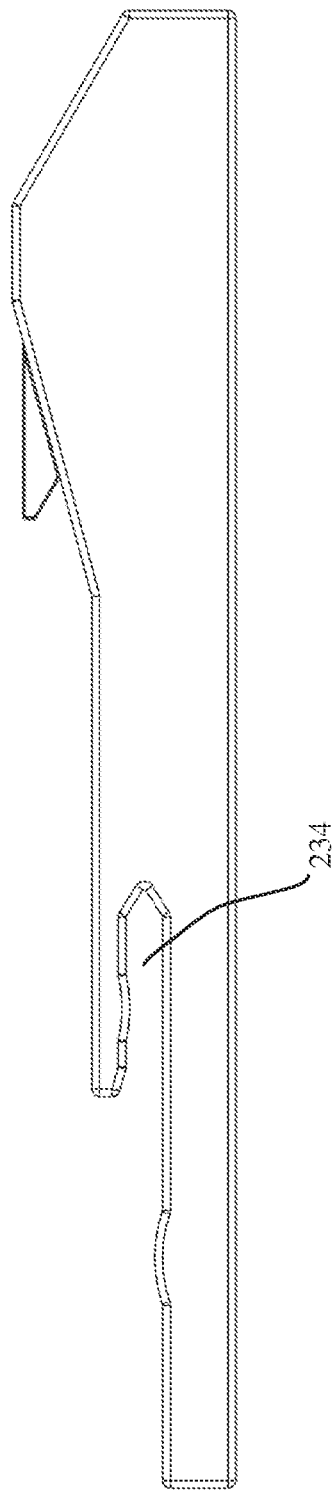
FIG. 11 is a rear view of the design shown in FIG. 1.
Figure 12:
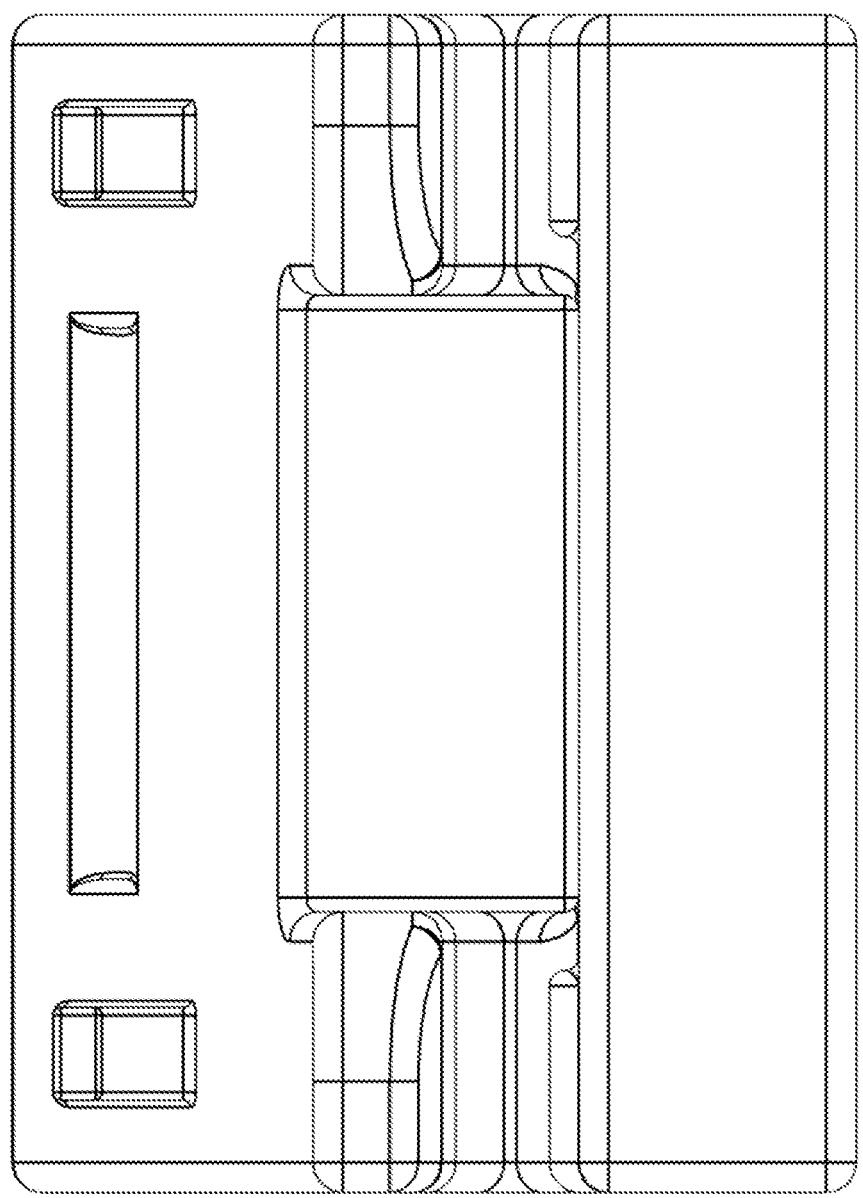
FIG. 12 is a right side view of the design shown in FIG. 1.
Figure 13:
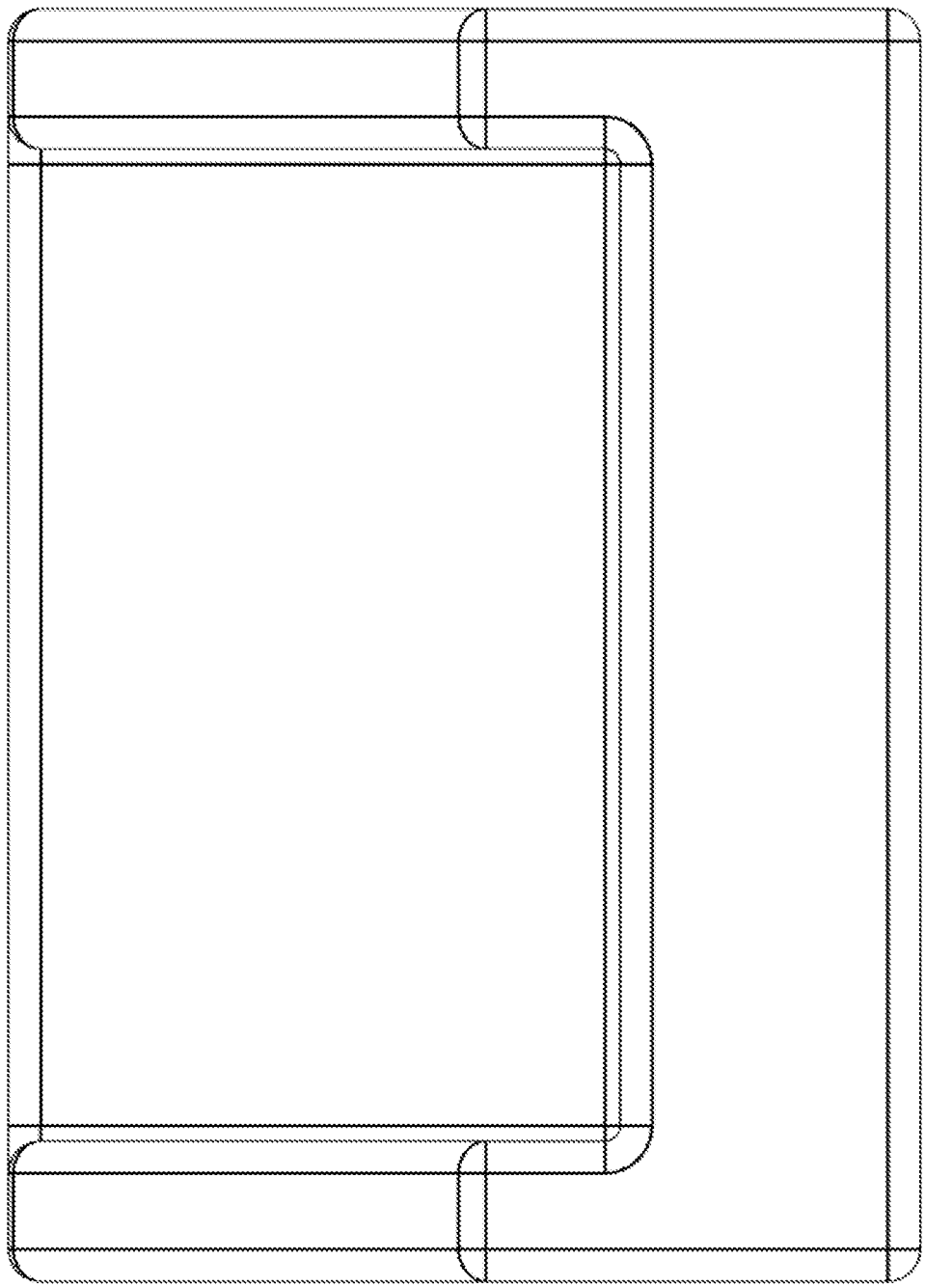
FIG. 13 is a left side view of the design shown in FIG. 1.
Figure 14:
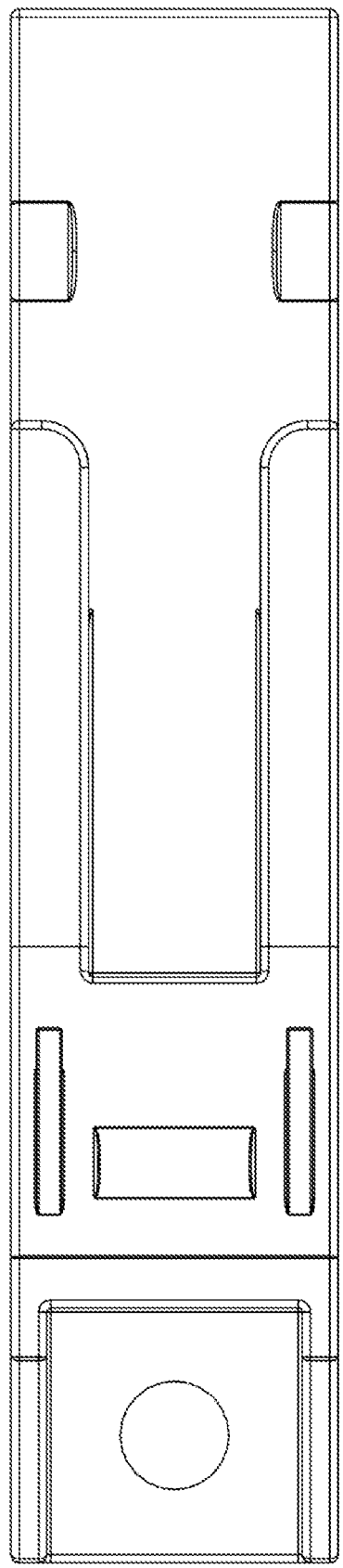
FIG. 14 is a top view of the design shown in FIG. 1.
Figure 15:
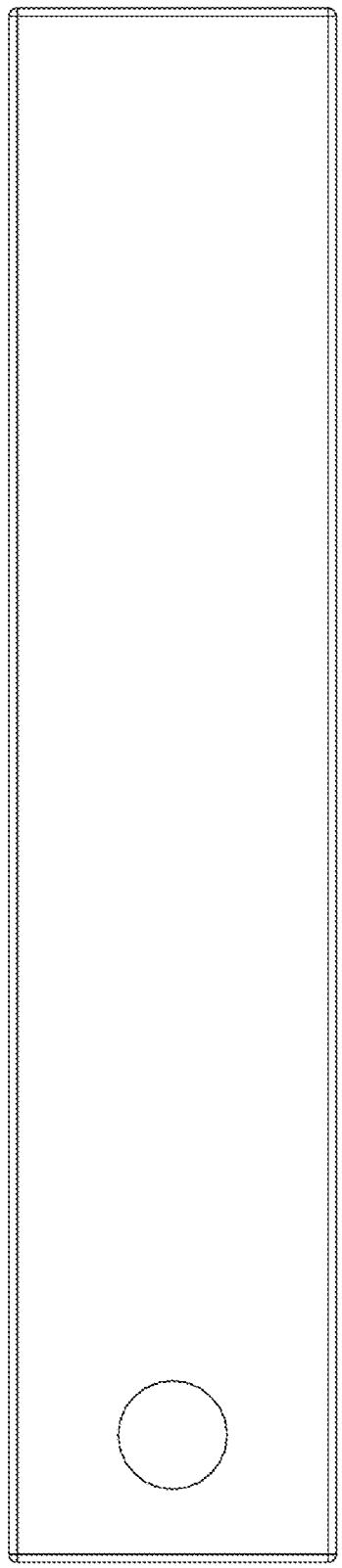
FIG. 15 is a bottom view of the design shown in FIG. 1.

FIG. 9 is perspective view of an example clamp mount 200. The clamp mount 200 may be used to removably mount the clamp 100 to a surface. The clamp mount 200 includes a body 210 having a flat bottom surface (e.g., surface 212 in FIG. 10). The clamp mount 200 includes an internal wall 220 defining a through hole in the flat bottom surface. A fastener (e.g., a nut or screw) may be passed through the through hole to fix the clamp mount 200 to the surface. The clamp mount 200 includes two guide rails 230 on a top surface of the body 210 defining a central slot 232 configured to receive a clamp (e.g., the pinch clamp 100). The clamp mount 200 may include a pair of keyed slots 234 within the two guide rails 230 configured to receive a pair of keyed projections 160 on the clamp 100. The keyed projections 160 may be located on opposite sides of the first rounded pinching surface 112. The keyed slots 234 may include one or more bumps or recesses to enhance an interference fit with a corresponding surface of the keyed projections 160. The clamp mount 200 may include guide projections 240 located on the top surface of the body 210. The guide projections 240 may correspond to guide indentations 162 (FIG. 7) of the clamp 100 to facilitate alignment of the clamp 100 and clamp mount 200. The projections and indentations may be reversed.

In some implementations, the body 210 of the clamp mount 200 includes a sloped surface 250 that engages the first end 130 of the clamp 100. The sloped surface 250 may include alignment tabs 252. The alignment tabs 252 may engage slots of the first member 110. The sloped surface 250 may include recess 254 configured to receive a curved portion of the first end 130 of the second member 120. For example, the curved portion of the second member 120 may form the pivot. By having a recess 254, the second member 120 may pivot with respect to the first member 110 when the first member 110 is attached to the clamp mount 200.

Figure 16:
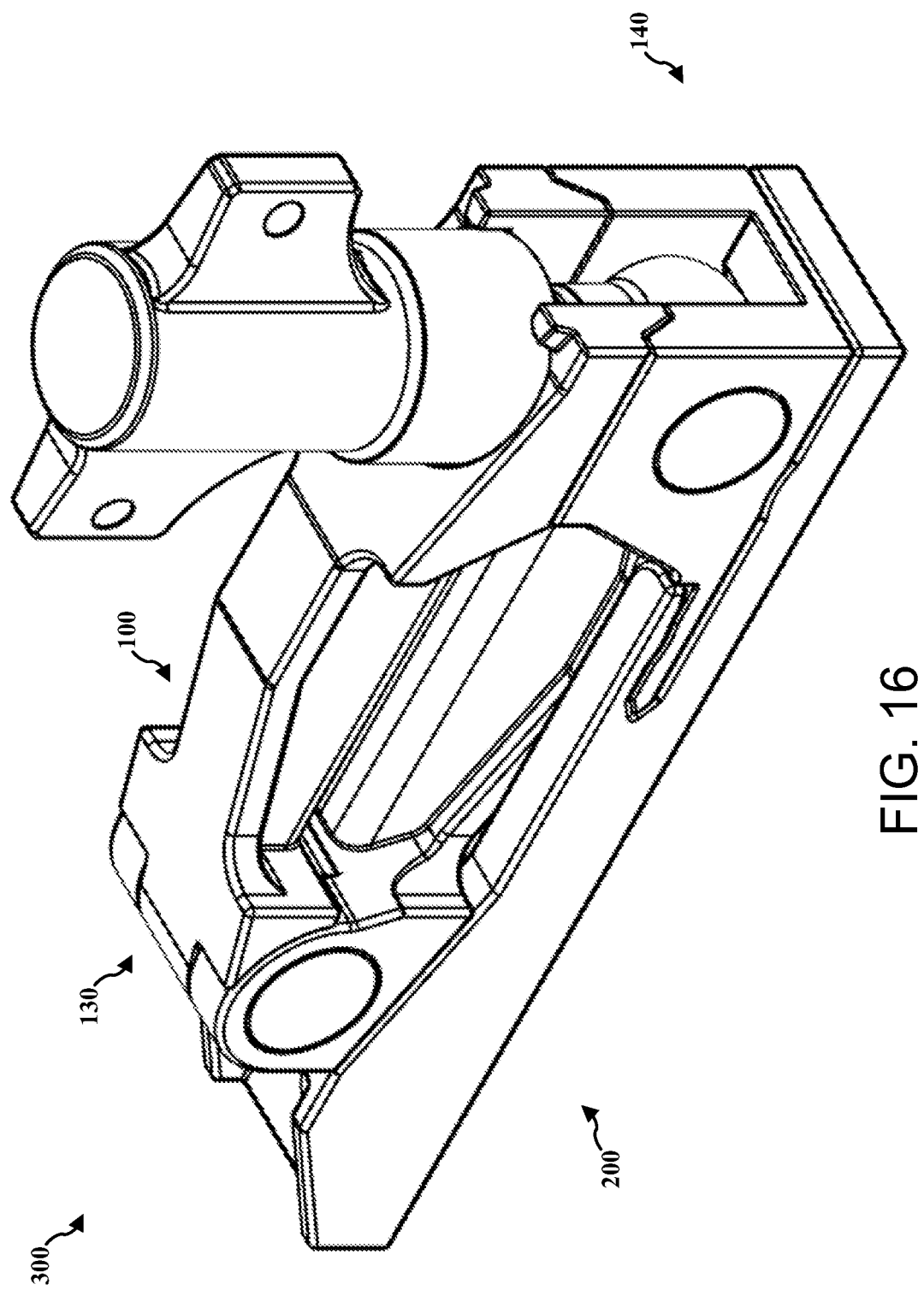
FIG. 16 is a perspective view of an example mounted pinch clamp, according to an aspect of the disclosure.

FIG. 16 is a perspective view of an example mounted pinch clamp 300. The mounted pinch clamp 300 may include the example pinch clamp 100 mounted to the example clamp mount 200. The first end 130 of the pinch clamp 100 may be slid into the central slot of the clamp mount 200. The keyed slots 234 may receive the keyed projections 160 and form an interference fit. The pinch clamp 100 may be removed by pulling the second end 140 directly away from the clamp mount 200.

Figure 17:
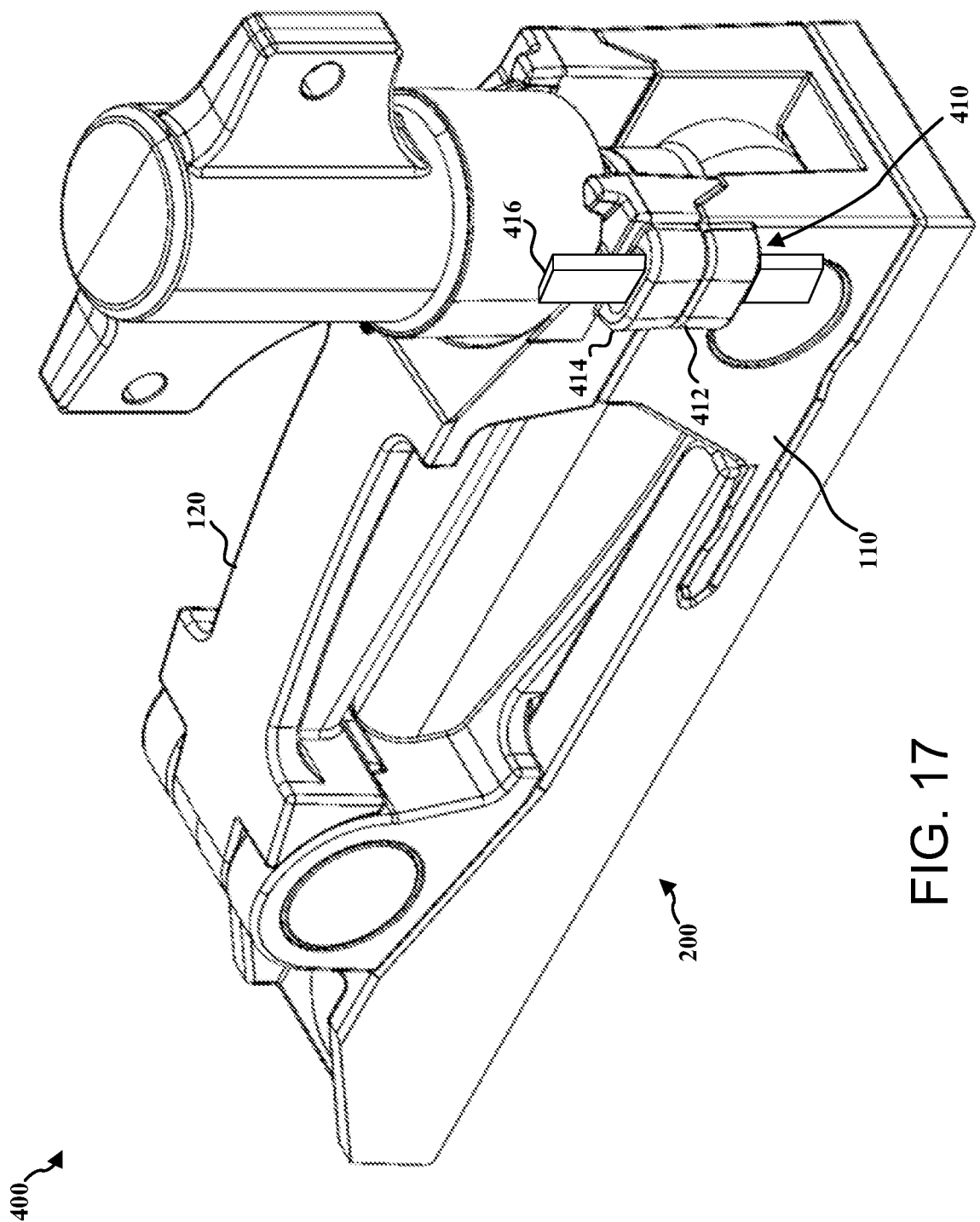
FIG. 17 is a perspective view of an example mounted pinch clamp with an additional lockout feature, according to an aspect of the disclosure.

FIG. 17 is a perspective view of an example mounted pinch clamp 400. The mounted pinch clamp 400 may be similar to the example pinch clamp 100 mounted to the example clamp mount 200. The mounted pinch clamp 400 further includes a locking feature 410. The locking feature 410 includes a first loop 412 that projects from a side of the first member 110 at the second end 140. The locking feature 410 includes a second loop 414 that projects from the same side of the second member 120 at the second end 140. The first loop 412 and the second loop 414 may align when the clamp 400 is in a closed position. A locking device 416 may be passed through the first loop 412 and the second loop 414 to help retain the clamp 400 in the closed position. The locking device 416 may be, for example, a zip tie or a shackle of a padlock.

Figure 18:
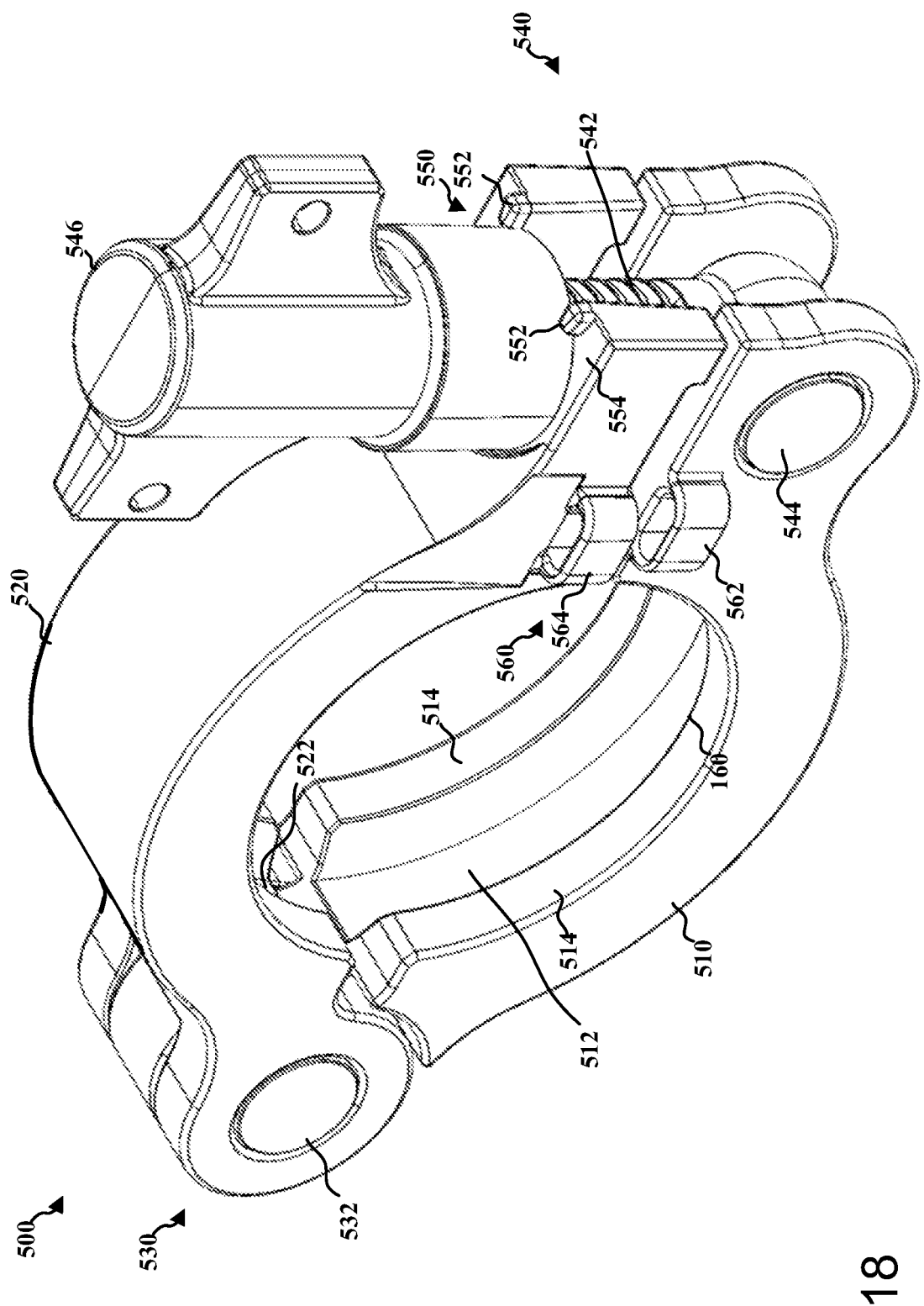
FIG. 18 is a perspective view of an example sanitary clamp with a lockout feature, according to an aspect of the disclosure.

FIG. 18 is a perspective view of an example sanitary clamp 500. Similar to the pinch clamp 100, the sanitary clamp 500 includes a first member 510 including an engagement surface 512. In contrast to the rounded pinching surface 112, the engagement surface 512 may be a channel defined by walls 514. The sanitary clamp 500 includes a second member 520 including a second engagement surface 522. The first member 510 and the second member 520 may be pivotably coupled at a first end 530 of the first member 510 and the second member 520. For example, the first member 510 may be coupled to the second member 520 via a pin 532 that passes through a respective opening in each of the first member 510 and the second member 520. Other example pivot mechanisms (e.g., hooks or protrusions) may be formed at the first end 530. The sanitary clamp 500 may include a threaded shaft 542 pivotably coupled to a second end 540 of the first member 510. For example, the threaded shaft 542 may be coupled to the first member 510 via a pin 544 or a structure of the first member 510 and/or the threaded shaft 542. In an aspect, a second end 540 of the second member 520 includes a seat 550 configured to receive the threaded shaft 542 and a nut 546 threaded onto the threaded shaft. For example, the seat 550 may include an end wall defining a U-shaped opening at the second end 540. In some implementations, the nut 546 may be a wing nut with handles to facilitate manual turning of the nut 546. The top surface of the seat 550 may include a partially annular flat surface 554 (similar to the surface 154 in FIG. 8) that contacts a bottom surface of the nut 546. The partially annular flat surface 554 and/or the bottom surface of the nut 546 may include corresponding textures (e.g., round depressions and projections) that resist movement when the nut 546 is fully tightened. The seat 550 may include inclined walls partially surrounding the partially annular flat surface to guide the nut 546 to the partially annular flat surface 554 as the nut is tightened on the threaded shaft. The seat 550 may include protrusions 552 at the second end 540 that prevent the nut 546 from sliding out of the seat 550 past the second end 540. For example, the protrusions 552 may extend upward from a top surface of the second member 520 on each side of the seat 550.

The sanitary claim 500 may retain the opposing flanged ends of two tubes and an optional gasket within the engagement surfaces 512, 522. The walls 514 may be sloped to draw the opposing flanges together as the clamp 500 is closed. The sanitary claim 500 may include a locking feature 560 that is similar to the locking feature 410. For example, the locking feature 560 may include a first loop 562 and a second loop 564 that can receive a locking member when the clamp 500 is in the closed position.

This written description uses examples to disclose aspects of the invention, including the preferred embodiments, and also to enable any person skilled in the art to practice the aspects thereof, including making and using any devices or systems and performing any incorporated methods. The patentable scope of these aspects is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. Aspects from the various embodiments described, as well as other known equivalents for each such aspect, can be mixed and matched by one of ordinary skill in the art to construct additional embodiments and techniques in accordance with principles of this application.

The invention claimed is:

1. A clamp and mount system comprising:
   a mount having a body, wherein the body further comprises a slot;
   a pinch clamp having:
   a first member including a first pinch surface;
   a second member having an opposing pinch surface and pivotably coupled to the first member at a first end of the first member; and
   a threaded shaft coupled to a second end of the first member,
   wherein a second end of the second member includes a seat configured such that the second member receives the threaded shaft and a nut threaded onto the threaded shaft, wherein the body further comprises a pair of keyed slots within two guide rails, and wherein the keyed slots receive keyed projections on the clamp.

2. The system of claim 1, further comprising corresponding guide indentations and guide projections located on a bottom surface of the first member and a top surface of the mount.

3. The system of claim 2, wherein the mount includes a sloped surface configured such that the sloped surface to receives the first end of the first member.

4. The system of claim 3, wherein the sloped surface includes alignment tabs and the first member includes slots configured to that receive the alignment tabs.

5. The system of claim 3, wherein the sloped surface includes a recess configured to such that the recess receives a curved portion of the first end of the second member.

6. The system of claim 1, wherein the first member includes a first loop projecting from a side of a second end of the first member, and the second member includes a second loop projecting from a same side of a second end of the second member, wherein the first loop and the second loop are aligned when the pinch clamp is in a closed position.

7. The system of claim 6, further comprising a locking device configured such that to the locking device extends through the first loop and the second loop.

8. The clamp and mount system of claim 1, wherein the threaded shaft is pivotably coupled to the second end of the first member.

9. The clamp and mount system of claim 8, wherein the seat including protrusions at the second end that prevent the nut from sliding out of the seat past the second end.

10. The clamp and mount system of claim 1, wherein the first and second pinch surfaces have a rounded profile.

11. The clamp and mount system of claim 1, wherein the seat further includes protrusions at the second end that prevent the nut from sliding out of the seat past the second end.

12. The system of claim 1, wherein the mount further comprises:
   an internal wall defining a through hole;
   the two guide rails defining the slot.

* * * * *